US012680118B2

(12) United States Patent　　(10) Patent No.:　US 12,680,118 B2
Priefert et al.　　　　　　　　　(45) Date of Patent:　　Jul. 14, 2026

(54) METHOD FOR PRODUCING A BIOMASS WHICH CAN BE EASILY BROKEN DOWN AND WHICH HAS AN INCREASED CONTENT OF POLYUNSATURATED FATTY ACIDS

(71) Applicant: EVONIK OPERATIONS GMBH, Essen (DE)

(72) Inventors: Horst Priefert, Ostbevern (DE); Jens Schneider, Bielefeld (DE); Joachim Windau, Warendorf (DE); Gabriel Závodský, Banska Bystrica (SK); Christian Rabe, Grossostheim (DE)

(73) Assignee: Evonik Operations GmbH, Essen (DE)

( * ) Notice: Subject to any disclaimer, the term of this patent is extended or adjusted under 35 U.S.C. 154(b) by 973 days.

(21) Appl. No.: 17/291,610

(22) PCT Filed: Nov. 7, 2019

(86) PCT No.: PCT/EP2019/080458
　　§ 371 (c)(1),
　　(2) Date: May 6, 2021

(87) PCT Pub. No.: WO2020/094751
　　PCT Pub. Date: May 14, 2020

(65) Prior Publication Data
　　US 2022/0017930 A1　　Jan. 20, 2022

(30) Foreign Application Priority Data
　　Nov. 9, 2018　(EP) ..................................... 18205303

(51) Int. Cl.
　　*C12P 7/6472*　　(2022.01)
　　*A23K 20/158*　　(2016.01)
　　*C12N 1/125*　　(2026.01)
　　*C12R 1/89*　　(2006.01)

(52) U.S. Cl.
　　CPC .......... *C12P 7/6472* (2013.01); *A23K 20/158* (2016.05); *C12N 1/125* (2021.05); *C12R 2001/89* (2021.05)

(58) Field of Classification Search
　　CPC ..... C12P 7/6472; A23K 20/158; C12N 1/125; C12R 2001/89
　　See application file for complete search history.

(56) References Cited

U.S. PATENT DOCUMENTS

| | | | |
|---|---|---|---|
| 5,130,242 A | 7/1992 | Barclay | |
| 7,736,884 B2 | 6/2010 | Gunnarsson | |
| 8,288,135 B2 | 10/2012 | Barclay | |
| 8,889,382 B2 * | 11/2014 | Luy | C12P 7/6472 435/243 |
| 9,738,851 B2 | 8/2017 | Ruecker et al. | |

| | | | |
|---|---|---|---|
| 9,848,623 B2 | 12/2017 | Bailey et al. | |
| 10,392,578 B2 | 8/2019 | Cherinko et al. | |
| 10,531,679 B2 | 1/2020 | Rudinger et al. | |
| 10,619,175 B2 | 4/2020 | Rabe et al. | |
| 10,842,174 B2 | 11/2020 | Durhuus et al. | |
| 10,844,316 B2 | 11/2020 | Sekiguchi et al. | |
| 11,261,400 B2 | 3/2022 | Bahl et al. | |
| 11,324,234 B2 | 5/2022 | Silva et al. | |
| 11,352,651 B2 | 6/2022 | Diehl et al. | |
| 11,414,621 B2 | 8/2022 | Heining et al. | |
| 11,464,244 B2 | 10/2022 | Rabe et al. | |
| 11,542,220 B2 | 1/2023 | Heining et al. | |
| 2011/0129884 A1 | 6/2011 | Luy | |
| 2013/0095537 A1 | 4/2013 | Kamada | |
| 2016/0249642 A1 | 9/2016 | Rabe et al. | |
| 2016/0319217 A1 | 11/2016 | Triplett et al. | |
| 2017/0290356 A1 | 10/2017 | Silva et al. | |
| 2017/0295823 A1 | 10/2017 | Rabe et al. | |
| 2017/0295824 A1 | 10/2017 | Priefert et al. | |
| 2017/0298318 A1 | 10/2017 | Rabe et al. | |
| 2019/0249108 A1 | 8/2019 | Cherinko et al. | |
| 2019/0300818 A1 | 10/2019 | Barz et al. | |
| 2019/0323043 A1 | 10/2019 | Diehl et al. | |
| 2020/0015500 A1 | 1/2020 | De Vriendt | |
| 2020/0231896 A1 | 7/2020 | Bahl et al. | |
| 2020/0231898 A1 | 7/2020 | Barz et al. | |
| 2020/0339498 A1 | 10/2020 | Heining et al. | |
| 2020/0362373 A1 | 11/2020 | Leininger et al. | |

(Continued)

FOREIGN PATENT DOCUMENTS

| | | |
|---|---|---|
| WO | WO 97/36996 | 10/1997 |
| WO | WO 97/37032 | 10/1997 |

(Continued)

OTHER PUBLICATIONS

Wu et al (Bioresource Technology 102 (2011) 1803-1807) (Year: 2011).*
Odiosolla dos Santos et al (Brazilian Journal of Microbiology (2012): 432-440) (Year: 2012).*
Nagano et al (Journal of Bioscience and Bioengineering vol. 116 No. 3, 337e339, 2013) (Year: 2013).*
Shabala et al (Mar Biotechnol (2013) 15:437-444) (Year: 2013).*
Taskin et al (Biofuels, Bioproducts and Biorefining (2015) vol. 9, issue 5: pp. 595-605) (Year: 2015).*

(Continued)

*Primary Examiner* — Thomas J. Visone
*Assistant Examiner* — Georgiana C Reglas
(74) *Attorney, Agent, or Firm* — Law Office of: Michael A. Sanzo, LLC

(57)　　　　ABSTRACT

According to the invention, it has been found that when the amount of sulfate used in the culturing of PUFAs-producing cells is selected such that the sulfate concentration drops to zero in the last phase of the growth phase of the cells, an easily disruptable biomass is obtained which has an increased proportion by mass of polyunsaturated fatty acids (PUFAs) in the final product.

19 Claims, No Drawings

(56)          References Cited

U.S. PATENT DOCUMENTS

| | | |
|---|---|---|
| 2020/0383353 A1 | 12/2020 | Wilson et al. |
| 2020/0404938 A1 | 12/2020 | Heining et al. |
| 2021/0017467 A1 | 1/2021 | Adugna et al. |
| 2021/0024966 A1 | 1/2021 | Heining et al. |
| 2021/0163842 A1 | 6/2021 | Heining et al. |
| 2021/0171991 A1 | 6/2021 | Burja et al. |
| 2021/0207056 A1 | 7/2021 | Heining et al. |
| 2021/0386095 A1 | 12/2021 | Erickson et al. |
| 2022/0017929 A1 | 1/2022 | Priefert et al. |
| 2023/0242836 A1 | 8/2023 | Diehl et al. |

FOREIGN PATENT DOCUMENTS

| | | |
|---|---|---|
| WO | WO 2014/122087 | 8/2014 |
| WO | WO 2014/122092 | 8/2014 |
| WO | WO 2019/122030 | 6/2019 |
| WO | WO 2020/123965 | 6/2020 |

OTHER PUBLICATIONS

Park et al (Appl Biol Chem (2017) 60(2):101-108) (Year: 2017).*
Bahafid et al (Industrial Applications, InTech, Nov. 8, 2017. Crossref, doi:10.5772/intechopen.70559) (Year: 2017).*
Prabu et al (Asian Biomedicine vol. 6 No. 5 Oct. 2012; 693-701) (Year: 2012).*
Yokochi et al. Optimization of docosahexaenoic acid production by Schizochytrium limacinum SR21. Appl Microbiol Biotechnol 49, 72-76 (1998) (Year: 1998).*
Papanikolaou and Aggelis. (2011). Lipids of oleaginous yeasts. Part II: Technology and potential applications. European Journal of Lipid Science . . . . https://doi.org/10.1002/EJLT.201100015 (Year: 2011).*
English language machine translation of the International Search Report for corresponding international application PCT/EP2019/080458, filed Nov. 7, 2019.
English language machine translation of the Written Opinion of the International Searching Authority for corresponding international application PCT/EP2019/080458, filed Nov. 7, 2019.
International Preliminary Report on Patentability for corresponding international application PCT/EP2019/080458, filed Nov. 7, 2019.
English language machine translation of the International Search Report for PCT/EP2019/080455 filed Nov. 7, 2019, for copending U.S. Appl. No. 17/291,608.
English language machine translation of the Written Opinion of the International Searching Authority for PCT/EP2019/080455 filed Nov. 7, 2019, for copending U.S. Appl. No. 17/291,608.
International Preliminary Report on Patentability for PCT/EP2019/080455 filed Nov. 7, 2019, for copending U.S. Appl. No. 17/291,608.
U.S. Appl. No. 15/027,429, filed Apr. 5, 2016, US-2016/0249642 A1, Sep. 1, 2016, Rabe.
U.S. Appl. No. 15/516,022, filed Mar. 31, 2017, US-2017/0295823 A1, Oct. 19, 2017, Rabe.
U.S. Appl. No. 15/516,023, filed Mar. 31, 2017, US-2017/0290356 A1, Oct. 12, 2017, Silva.
U.S. Appl. No. 15/516,024, filed Mar. 31, 2017, US-2017/0295824 A1, Oct. 19, 2017, Priefert.
U.S. Appl. No. 15/516,038, filed Mar. 31, 2017, US-2017/0298318 A1, Oct. 19, 2017, Rabe.
U.S. Appl. No. 16/309,632, filed Dec. 13, 2018, US-2019/0249108 A1, Aug. 15, 2019, Cherinko.
U.S. Appl. No. 16/317,249, filed Jan. 11, 2019, US-2019/0300818 A1, Oct. 3, 2019, Bärz.
U.S. Appl. No. 16/317,305, filed Jan. 11, 2019, US-2020/0231898 A1, Jul. 23, 2020, Bärz.
U.S. Appl. No. 16/473,805, filed Jun. 26, 2019, US-2019/0323043 A1, Oct. 24, 2019, Diehl.

U.S. Appl. No. 16/639,529, filed Feb. 14, 2020, US-2021/0171991 A1, Jun. 10, 2021, Burja.
U.S. Appl. No. 16/644,443, filed Mar. 4, 2020, US-2020/0231896 A1, Jul. 23, 2020, Bahl.
U.S. Appl. No. 16/469,286, filed Jun. 13, 2019, US-2020/0015500 A1, Jan. 16, 2020, De Vriendt.
U.S. Appl. No. 16/636,940, filed Feb. 6, 2020, US-2020/0362373 A1, Nov. 19, 2020, Leininger.
U.S. Appl. No. 16/886,691, filed May 28, 2020, US-2020/0383353 A1, Dec. 10, 2020, Wilson.
U.S. Appl. No. 16/956,453, filed Jun. 19, 2020, US-2020/0339498 A1, Oct. 29, 2020, Heining.
U.S. Appl. No. 16/956,820, filed Jun. 22, 2020, US-2020/0404938 A1, Dec. 31, 2020, Heining.
U.S. Appl. No. 17/042,788, filed Sep. 28, 2020, US-2021/0024966 A1, Jan. 28, 2021, Heining.
U.S. Appl. No. 17/042,791, filed Sep. 28, 2020, US-2021/0017467 A1, Jan. 21, 2021, Adugna.
U.S. Appl. No. 17/055,047, filed Nov. 12, 2020, NA, NA, Heining.
U.S. Appl. No. 17/055,083, filed Nov. 12, 2020, US-2021/0163842 A1, Jun. 3, 2021, Heining.
U.S. Appl. No. 17/284,463, filed Apr. 10, 2021, NA, NA, Erickson.
U.S. Appl. No. 17/291,608, filed May 6, 2021, NA, NA, Priefert.
EPO English language machine translation of the description and claims for corresponding RU 2326171, filed Jun. 10, 2008.
EPO English language machine translation of the description and claims for corresponding RU 2336307, filed Oct. 20, 2008.
Restriction Requirement mailed Jun. 16, 2023 for copending U.S. Appl. No. 17/291,608.
Response to Restriction Requirement filed Aug. 12, 2023 for copending U.S. Appl. No. 17/291,608.
Amendment to Accompany Response to Restriction Requirement filed Aug. 12, 2023 for copending U.S. Appl. No. 17/291,608.
Non Final Office Action mailed Oct. 16, 2023 for copending U.S. Appl. No. 17/291,608.
Amendment & Response to Non Final Office Action filed Jan. 7, 2024 for copending U.S. Appl. No. 17/291,608.
Final Office Action mailed Apr. 10, 2024 for copending U.S. Appl. No. 17/291,608.
U.S. Appl. No. 18/010,795, filed Dec. 15, 2022, US-2023/0242836 A1, Aug. 3, 2023, Diehl.
Amendment & Response to Final Office Action filed Jul. 5, 2024 for copending U.S. Appl. No. 17/291,608.
RCE to Accompany Response to Final Office Action filed Jul. 5, 2024 for copending U.S. Appl. No. 17/291,608.
Kavitha, et al., "Culture media optimization of Porphyridium purpureum: production potential of biomass, total lipids, arachidonic and eicosapentaenoic acid," J. Food Sci. Technol. 53(5):2270-2278 May 2016.
Prabu, et al., "Effect of sodium sulphate salinity for production of docosahexaenoic acid (DHA) by Thraustochytrids aureum RAK-21," Asian Biomedicine 6(5):693-701 (Oct. 2012).
Unagul, et al., "Biomass and docosahexaenoic acid formation by Schizochytrium mangrovei Sk-02 at low salt concentrations," Botanica Marina 49:182-190 (2006).
Non Final Office Action mailed Oct. 23, 2024 for copending U.S. Appl. No. 17/291,608.
Amendment & Response to Office Action filed Jan. 17, 2025 for copending U.S. Appl. No. 17/291,608.
CN Office Action dated Dec. 24, 2024 from corresponding Chinese examination proceedings for CN 201980073209 with an English language translation of text of the decision of rejection attached.
Wang, et al., "Process Optimization," Pharmaceutical Technology, 1st Edition, China Press of Chinese Medicine, pp. 354-355 (2009) with English language translation attached.
Chi, et al., "Production of polyunsaturated fatty acids by Schizochytrium (Aurantiochytrium) spp.," Biotechnology Advances 55:107897 (available online Dec. 2021).
Final Office Action mailed Apr. 11, 2025 for copending U.S. Appl. No. 17/291,608.

(56)  References Cited

OTHER PUBLICATIONS

Notice of Appeal filed Jul. 7, 2025 for for copending U.S. Appl. No. 17/291,608.

Response Under 37 CFR § 1.116 filed Jul. 7, 2025 for for copending U.S. Appl. No. 17/291,608.

* cited by examiner

METHOD FOR PRODUCING A BIOMASS WHICH CAN BE EASILY BROKEN DOWN AND WHICH HAS AN INCREASED CONTENT OF POLYUNSATURATED FATTY ACIDS

CROSS REFERENCE TO RELATED APPLICATIONS

The present application is US national stage of international application PCT/EP2019/080458, which had an international filing date of Nov. 7, 2019 and which priority to EP 18205303.3, filed on Nov. 9, 2018. These prior applications are hereby incorporated by reference herein in their entirety.

The present invention relates to a process for producing an easily disruptable biomass having an increased content of polyunsaturated fatty acids and to a biomass obtainable by said process. Processes for producing biomass containing polyunsaturated fatty acids (PUFAs) have already been described in the prior art. What are frequently used here are the Labyrinthulomycetes, which naturally accumulate polyunsaturated fatty acids as storage lipids in a relatively large amount in the cell.

These microalgae grow naturally in seawater, meaning that culturing of the microalgae was initially done in media having a high chloride content. However, high chloride contents are unsuitable for culturing in steel bioreactors, since they cause corrosion of the metal.

Therefore, fermentation media having a low chloride content and, instead, a high sulfate content have been described in the prior art as alternative fermentation media.

However, in this case, the algae biomass obtained generally has a limited content of PUFAs, possibly because the high sulfate amount means that the proportion of cell wall formed in the final product is relatively high at the expense of the amount of PUFAs present. Moreover, because of the high sulfate content, the cell wall is quite stable, and this makes oil release from the cells difficult.

According to the invention, it has been found that, surprisingly, the relative proportion of PUFAs formed can be distinctly increased by limitation of the sulfate content during fermentation and that oil release from the cells can be distinctly facilitated by the simultaneously achieved reduction in the stability of the cell wall, it being possible to destabilize the cell wall by sulfate limitation to the extent that oil release from the cells can be achieved without great expenditure of mechanical force.

It is therefore an object of the present invention to provide a process for providing a biomass containing PUFAs, in which the biomass obtained has an increased proportion by mass of PUFAs in the final product and, at the same time, the release of the PUFAs present from the final product is facilitated. At the same time, it is intended that preferably a non-corrosive fermentation medium be able to be used in the process.

The object of the invention is achieved by a process for producing a biomass containing PUFAs, characterized in that the biomass is produced by culturing the PUFAs-producing cells in a fermentation medium where the sulfate content is adjusted such that the sulfate content falls to zero in the last phase of fermentation.

Processes according to the invention preferably comprise a growth phase and a subsequent oil-production phase for the purpose of optimizing oil production. What takes place in the opening growth phase is firstly the culturing and the increase in biomass of the PUFAs-producing cells present in the fermentation medium—with maximum suppression of oil production—with the result that a highest possible biomass density is set in the medium, whereas what takes place in the subsequent oil-production phase, which is generally introduced by specific measures, is predominantly oil production by the cells of the biomass, with the growth of the cells being stopped at least as far as possible. This means that, in the oil-production phase, the increase in biomass is at least primarily attributable not to an increase in cell count, but to the accumulation of lipids in the cell interior of the cells present. The growth of the cells in the growth phase is made possible by provision of optimal growth conditions, whereas the transition into the oil-production phase can be introduced by limitation of individual or multiple limiting factors, especially nutrient components such as, for example, nitrogen sources.

According to the invention, "last phase of fermentation" is preferably understood to mean the oil-production phase.

Processes according to the invention are preferably distinguished by the sulfate concentration in the fermentation medium falling to zero in the second half of the growth phase, preferably in the last eighth of the growth phase and particularly preferably just before the start of the oil-production phase.

The present invention further provides biomasses, preferably those containing cells of the Thraustochytriaceae family, which are obtainable by processes according to the invention. What has been found to be particularly advantageous according to the invention is specifying the sulfate content in the medium such that there is a final sulfate concentration in the biomass obtained of 7 to 10 g per kg of biomass. The cells then still have sufficient stability to protect the PUFAs present from undesired oxidative degradation. In this connection, the amount of sulfate to be added can be easily calculated because the sulfate added is completely assimilated by the cells. In this way, what is obtained is a biomass which is easily disruptable, but still sufficiently stable in order to be able to be transferred into a dry biomass. Because of the relatively unstable cell wall, biomasses according to the invention can accordingly be preferably broken with use of low mechanical forces, preferably just with use of a force action of up to 12 Wh/kg, particularly preferably up to 10 or 8 Wh/kg, in particular 1 to 12 Wh/kg, 1 to 10 Wh/kg or 2 to 8 Wh/kg. The present invention similarly further provides a biomass which is obtainable using a process according to the invention.

The present invention therefore particularly further provides a biomass containing PUFAs that has a sulfate content of 7 to 10 g of sulfate, preferably 7.5 to 9.5 g of sulfate, per kg of biomass. According to the invention, "sulfate content" is to be understood to mean the total content of sulfate, i.e. the content of free and bound, in particular organically bound, sulfate, in relation to the biomass. It can be assumed that the majority of the sulfate present in the biomass is present as a constituent of exopolysaccharides, which are involved in the formation of the cell wall of microorganisms.

According to the invention, the sulfate content is preferably determined by ascertaining the sulfur content of the biomass obtained, since the majority of the sulfur present in the biomass can be attributed to the sulfate present. Sulfur which can be attributed to other sources can be disregarded owing to the amount of sulfate present. Thus, the amount of sulfate present can be readily ascertained from the amount of sulfur ascertained.

In this connection, the sulfur content of the biomass is preferably determined by elemental analysis in accordance with DIN EN ISO 11885. To analyse the sulfur content of the biomass, suitable aliquots of the sample are disrupted before the analysis, preferably using nitric acid and hydrogen peroxide at 240° C. under pressure, so as to ensure that the sulfur which is present is readily available.

According to the invention, "biomass", "dry biomass", "biomass of PUFAs-producing cells" or "dry biomass of PUFAs-producing cells" is generally to be understood to mean the determinable dry biomass.

In this context, the amount of dry biomass present in a sample is preferably determined as follows: A homogeneous sample is collected and is centrifuged to separate off the liquid constituents.

Thereafter, the biomass obtained by centrifugation is washed with water in order to dissolve salts and any further soluble constituents and is then centrifuged again. The dry biomass thus obtained is lastly dried overnight in a drying cabinet. In this context, the percentage of dry biomass present in the sample arises from the quotient between mass of determined dry biomass after drying and initial mass of the investigated sample. The dry biomass thus ascertained also additionally comprises the oil formed by the biomass.

The fat proportion present in the dry biomass is preferably determined by uptake of the dry biomass in a methanol/chloroform solution and subsequent ultrasound treatment of the sample thus obtained. The sample thus obtained is subsequently saponified with potassium hydroxide and acidified using hydrochloric acid. Thereafter, the free fatty acids are methylated using BF3 (30% boron trifluoride in methanol) and separated by means of partition chromatography with a temperature gradient. Detection is then carried out by means of flame ionization detection (FID).

According to the invention, "lipid-free biomass" is accordingly to be understood to mean the dry biomass minus the fat proportion thus ascertained.

According to the invention, the desired sulfate concentration in the medium can be adjusted in different ways.

According to the invention, what is essential is that the sulfate concentration falls to zero in the course of fermentation, the sulfate concentration falling to zero preferably in the second half of the growth phase and particularly preferably in the last eighth of the period of the growth phase. In this context, it is particularly preferred when the sulfate concentration falls to zero just before the start of the oil-production phase, particularly up to 3 hours, preferably up to 2 hours and above all up to one hour before the start of the oil-production phase. This can be easily achieved by the required amount of sulfate already being initially charged in full in the starting medium at the start of fermentation (so-called batch process). The amount of sulfate required can be easily calculated, since the cells used to form the biomass completely assimilate the sulfate added in a relatively small amount.

When using a so-called fed-batch process, the amount of sulfate required may alternatively be metered in during the course of fermentation or, accordingly, some of the sulfate may be initially charged and the remainder metered in during the course of fermentation.

Especially when it emerges during the course of fermentation that the amount of biomass produced exceeds the originally calculated value, it is possible to ensure by subsequent metering-in of sulfate that the resulting biomass has sufficient cell stability in order to prevent premature oil release. In a preferred embodiment, the sulfate amount in the starting medium is selected such that the sulfate concentration is above the saturation concentration of the cells at least during the first 30% of the period of the growth phase of the cells, preferably at least during the first 40%, 50% or 60% and particularly during the first 70%, 80% or 90% of the period of the growth phase of the cells. In this context, the sulfate concentration is preferably at least 5 g of sulfate per kg of lipid-free biomass during the specified phase.

According to the invention, the sulfate salt used is preferably sodium sulfate, ammonium sulfate or magnesium sulfate and also mixtures thereof. According to the invention, the feeding of the sulfate can, alternatively or additionally, also be done through the use of industrial raw materials which are contaminated or supplemented with sulfate.

According to the invention, it has been further found that, surprisingly, the lowering of the sulfate concentration can also be combined with low chloride concentrations, meaning that the biomass can be obtained using a non-corrosive fermentation medium.

A process according to the invention is therefore preferably further distinguished by the fermentation medium used according to the invention having a chloride concentration of less than 1 g/l, particularly less than 500 mg/l and preferably less than 250 mg/l during the entire fermentation. Biomasses according to the invention preferably have a chloride content of not more than 2 g per kg of biomass, particularly 0.5 to 1.8 g and particularly preferably 0.5 to 1.5 g per kg of biomass. According to the invention, "chloride content" is understood to mean the amount of determinable chlorine. The amount of chlorine present can, for example, be determined by elemental analysis in accordance with DIN EN ISO 11885. Chlorine is present in the biomass in the form of salts, which are called "chlorides". When the present application mentions "chlorides" or "chloride ions", what is always meant is only the amount of chloride or detectable chlorine, and not the amount of chloride salts, which always also comprise cationic counterions besides the chloride ion.

The PUFAs-producing cells are preferably cells which already naturally produce PUFAs; however, they can also be cells made capable of producing PUFAs by means of appropriate gene-technology methods. Production can, in this context, be autotrophic, mixotrophic or heterotrophic.

The biomass according to the invention accordingly comprises such cells and preferably substantially consists of such cells.

Preferably, the cells are those which produce PUFAs heterotrophically. According to the invention, the cells preferably take the form of algae, fungi, in particular yeasts, or protists. Particularly preferably, the cells are microorganisms, in particular microbial algae or fungi.

Suitable cells of oil-producing yeasts are, in particular, strains of *Yarrowia*, *Candida*, *Rhodotorula*, *Rhodosporidium*, *Cryptococcus*, *Trichosporon* and *Lipomyces*.

A biomass according to the invention preferably comprises cells of the taxon Labyrinthulomycetes (Labyrinthulea), in particular those of the family of the Thraustochytriaceae. The family of the Thraustochytriaceae includes the genera *Althornia*, *Aplanochytrium*, *Elina*, *Japonochytrium*, *Schizochytrium*, *Thraustochytrium*, *Aurantiochytrium*, *Oblongichytrium* and *Ulkenia*. Particular preference is given to cells of the genera *Thraustochytrium*, *Schizochytrium*, *Aurantiochytrium* or *Oblongichytrium*, especially those of the genus *Aurantiochytrium*. A particularly preferred strain is the strain *Aurantiochytrium limacinum* SR21 (IFO 32693).

The biomass according to the invention preferably takes the form of the product of a fermentative culturing process. Accordingly, the biomass may contain not only the cells to be disrupted but also constituents of the fermentation medium. These constituents may take the form of, in particular, salts, antifoam agents and unreacted carbon source and/or nitrogen source. The cell content in this biomass is preferably at least 70% by weight, preferably at least 75% by weight. Optionally, the cell content in the biomass may be increased by suitable wash steps to, for example, at least 80 or at least 90% by weight before carrying out the cell disruption process. However, the biomass obtained may also be used directly in the cell disruption process.

The cells in the biomass are preferably distinguished by the fact that they contain at least 20% by weight, preferably at least 30% by weight, in particular at least 40% by weight, of PUFAs, based in each case on the cell dry mass.

In a preferred embodiment, the majority of the lipids is present in the form of triglycerides, with preferably at least 50% by weight, in particular at least 75% by weight and, in an especially preferred embodiment, at least 90% by weight of the lipids present in the cell being present in the form of triglycerides.

Preferably, at least 10% by weight, in particular at least 20% by weight, especially preferably 20 to 60% by weight, in particular 20 to 40% by weight, of the fatty acids present in the cell are PUFAs. According to the invention, polyunsaturated fatty acids (PUFAs) are understood to mean fatty acids having at least two C—C double bonds. According to the invention, highly unsaturated fatty acids (HUFAs) are preferred among the PUFAs. According to the invention, HUFAs are understood to mean fatty acids having at least four C—C double bonds.

The PUFAs may be present in the cell in free form or in bound form. Examples of the presence in bound form are phospholipids and esters of the PUFAs, in particular monoacyl-, diacyl- and triacylglycerides. In a preferred embodiment, the majority of the PUFAs is present in the form of triglycerides, with preferably at least 50% by weight, in particular at least 75% by weight and, in an especially preferred embodiment, at least 90% by weight of the PUFAs present in the cell being present in the form of triglycerides.

Preferred PUFAs are omega-3 fatty acids and omega-6 fatty acids, with omega-3 fatty acids being especially preferred. Preferred omega-3 fatty acids in this context are eicosapentaenoic acid (EPA, 20:5ω-3), in particular (5Z,8Z, 11Z,14Z,17Z)-eicosa-5,8,11,14,17-pentaenoic acid, and docosahexaenoic acid (DHA, 22:6ω-3), in particular (4Z, 7Z,10Z,13Z,16Z,19Z)-docosa-4,7,10,13,16,19-hexaenoic acid, with docosahexaenoic acid being especially preferred. Processes for producing the PUFAs-containing cells especially of the order Thraustochytriales have been described in detail in the prior art (see, for example, WO91/07498, WO94/08467, WO97/37032, WO97/36996, WO01/54510). Production generally takes place by cells being cultured in a fermenter in the presence of a carbon source and of a nitrogen source. In this context, biomass densities of more than 100 grams per litre and production rates of more than 0.5 gram of lipid per litre per hour may be attained. The process is preferably carried out as a so-called fed-batch process, i.e. the carbon source and possibly also the nitrogen and phosphate sources are fed in incrementally during the fermentation. Once the desired biomass has been reached, lipid production may be induced by various measures, for example by limiting the nitrogen source, the phosphate source or the oxygen content or combinations thereof.

Suitable carbon sources are both alcoholic and non-alcoholic carbon sources. Examples of alcoholic carbon sources are methanol, ethanol and isopropanol. Examples of non-alcoholic carbon sources are fructose, glucose, sucrose, molasses, starch and corn syrup, and also organic acids such as acetic acid, propionic acid and medium- and long-chain fatty acids and the salts thereof. Processes preferred according to the invention are distinguished by at least one carbon source being continuously metered into the medium during the complete fermentation process.

Suitable nitrogen sources are both inorganic and organic nitrogen sources. Examples of inorganic nitrogen sources are nitrates and ammonium salts, in particular ammonium sulfate and ammonium hydroxide. Examples of organic nitrogen sources are amino acids, in particular glutamate, and urea.

According to the invention, the introduction of the oil-production phase is preferably carried out as described in WO 01/54510, by limiting at least one limiting nutrient component, preferably by limiting at least one nitrogen source.

In addition to sulfates and any chlorides used, it is also optionally possible during fermentation to use further salts, especially those selected from sodium carbonate, sodium hydrogen carbonate, soda ash or inorganic phosphorus compounds. If further salts are used, these are preferably each used in an amount of less than 12 g/l, particularly less than 8 g/l and particularly preferably less than 5 g/l. The total salt content in the fermentation medium is preferably 5 to 30 g/l, particularly 10 to 20 g/l, at the start of the main fermentation.

In addition, organic phosphorus compounds and/or known growth-stimulating substances, such as, for example, yeast extract or corn steep liquor, may also be added so as to have a positive effect on the fermentation.

The cells are fermented preferably at a pH of 4 to 11, particularly 6 to 10, and preferably at a temperature of at least 20° C., particularly 20° C. to 40° C. and particularly preferably at least 30° C. A typical fermentation process takes up to approximately 100 hours.

According to the invention, the cells are preferably fermented up to a biomass density of at least 50, 60 or 70 g/l, particularly 50 to 250 g/l or 60 to 220 g/l, preferably at least 80 or 90 g/l, particularly 80 to 200 g/l, particularly preferably at least 100 g/l and particularly 100 to 180 g/l. In this context, the data are based on the content of dry biomass in relation to the total volume of the fermentation broth after completion of fermentation. The content of dry biomass is determined by filtration of the biomass from the fermentation broth, subsequent washing with water and then complete drying—for example in a microwave—and lastly ascertainment of the dry weight. In one embodiment preferred according to the invention, the sulfate concentration falls to zero just before the start of the oil-production phase, preferably after a biomass density of at least 50 g, particularly preferably at least 80, 100, 120 or 140 g, per litre of fermentation medium has been reached.

After harvesting the cells or optionally even shortly before harvesting the cells, the cells are preferably pasteurized in order to kill the cells and to inactivate enzymes which might promote lipid degradation.

After completion of fermentation, the fermentation broth obtained can be subjected to an oil-isolation method, directly or optionally after prior concentration, in order to extract the oil present. Such oil-isolation methods are, for example, described in WO 01/53512 and WO 2011/153246. Alternatively, after completion of fermentation, the biomass containing PUFAs can also be harvested. To this end, the fermentation broth is preferably also first concentrated.

According to the invention, the fermentation broth is preferably concentrated by centrifugation, filtration, decanting and/or solvent evaporation in order to first separate off most of the fermentation medium from the biomass. Solvent evaporation is preferably achieved using a drum dryer, a tunnel dryer, by means of spray drying or vacuum evaporation. In particular, solvent evaporation may also be achieved using a rotary evaporator, a thin-film evaporator or a falling-film evaporator. A suitable alternative to solvent evaporation is, for example, reverse osmosis for concentrating the fermentation broth.

To obtain the biomass, the concentrated fermentation broth thus obtained is preferably further dried, preferably by fluidized bed granulation. Preferably, the moisture content of the biomass is reduced to below 15% by weight, particularly to below 10% by weight and particularly preferably to below 5% by weight by the subsequent drying process.

After harvesting the cells or optionally even shortly before harvesting the cells, the cells are preferably pasteurized in order to kill the cells and to inactivate enzymes which might promote lipid degradation.

In one embodiment particularly preferred according to the invention, the biomass is dried in accordance with the invention in a fluidized bed granulation process or a nozzle spray drying process, as described in WO 2015/052048 for example.

During the drying process, silica may optionally be added to the biomass as anti-caking agent so that the biomass can be converted to an easier-to-manage state. For this purpose, the fermentation broth comprising biomass and also the silica are preferably sprayed into the particular drying zone. Alternatively, the biomass is preferably mixed with the silica only after the drying process. In this regard, reference is also made in particular to the patent application WO 2015/052048.

In a preferred embodiment, a biomass to be used according to the invention has a concentration of silica, in particular hydrophilic or hydrophobic silica, of 0.2 to 10% by weight, in particular 0.5 to 5% by weight, especially 0.5 to 2% by weight, after the drying process.

A free-flowing, fine-grained or coarse-grained product, preferably a granulate, is preferably obtained by the drying process. A product having the desired particle size can optionally be obtained from the granulate obtained by sieving or dust separation.

Providing a free-flowing, fine-grained powder was obtained, this can optionally be converted into a coarse-grained, readily free-flowing and largely dust-free product, which can be stored, by suitable compacting or granulating processes.

Conventional organic or inorganic auxiliaries or supports such as starch, gelatin, cellulose derivatives or similar substances, which are typically used in food processing or feed processing as binding agents, gelling agents or thickeners, may optionally be used in this subsequent granulation or compacting process.

According to the invention, "free-flowing" is to be understood to mean a powder which can flow out unhindered from a series of glass flow-out vessels having differently sized outlet openings, at least from the vessel having a 5 millimetre opening (Klein: Seifen, Öle, Fette, Wachse 94, 12 (1968)).

According to the invention, "fine-grained" is to be understood to mean a powder having a predominant fraction (>50%) of particle sizes of 20 to 100 micrometres in diameter.

According to the invention, "coarse-grained" is to be understood to mean a powder having a predominant fraction (>50%) of particle sizes of 100 to 2500 micrometres in diameter.

According to the invention, "dust-free" is to be understood to mean a powder containing only low fractions (<10%, preferably <5%) of particle sizes below 100 micrometres.

Particle sizes are preferably determined according to the invention by laser diffraction spectrometric methods. Usable methods are described in the textbook "Teilchengrößenmessung in der Laborpraxis" [Particle size measurement in laboratory practice] by R. H. Müller and R. Schuhmann, Wissenschaftliche Verlagsgesellschaft Stuttgart (1996) and in the textbook "Introduction to Particle Technology" by M. Rhodes, Wiley & Sons (1998). Inasmuch as various methods can be used, the first-cited usable method from the textbook by R. H. Müller and R. Schuhmann for the measuring of particle size is preferably used.

The products obtained by drying processes according to the invention preferably have a fraction of at least 80% by weight, particularly at least 90% by weight, particularly preferably at least 95% by weight, of particles having a particle size of 100 to 3500 micrometres, preferably 100 to 3000 micrometres, above all 100 to 2500 micrometres.

The products of a fluidized bed granulation process obtained according to the invention preferably have in this case a fraction of at least 80% by weight, particularly at least 90% by weight, particularly preferably at least 95% by weight, of particles having a particle size of 200 to 3500 micrometres, preferably 300 to 3000 micrometres, above all 500 to 2500 micrometres.

The products of a spray drying process obtained according to the invention preferably have in contrast a fraction of at least 80% by weight, particularly at least 90% by weight, particularly preferably at least 95% by weight, of particles having a particle size of 100 to 500 micrometres, preferably 100 to 400 micrometres, above all 100 to 300 micrometres.

The products of a spray drying process and subsequent granulation process obtained according to the invention preferably have a fraction of at least 80% by weight, particularly at least 90% by weight, particularly preferably at least 95% by weight, of particles having a particle size of 100 to 1000 micrometres.

The fraction of dust, i.e. particles having a particle size of less than 100 micrometres, is preferably at most 10% by weight, particularly at most 8% by weight, particularly preferably at most 5% by weight, above all at most 3% by weight.

The bulk density of the products according to the invention is preferably from 400 to 800 kg/m$^3$, particularly preferably from 450 to 700 kg/m$^3$.

The present invention therefore also further provides a feedstuff comprising a biomass according to the invention and also further feedstuff ingredients.

In this connection, the further feedstuff ingredients are preferably selected from protein-containing, carbohydrate-containing, nucleic-acid-containing and lipid-soluble components and, if appropriate, further fat-containing components and furthermore from among other additives such as minerals, vitamins, pigments and amino acids. In addition, structurants may also be present, besides nutrients, for example so as to improve the texture or the appearance of the feedstuff. Furthermore, it is also possible to use, for example, binders so as to influence the consistency of the feedstuff. A component which is preferably employed and which constitutes both a nutrient and a structurant is starch.

According to the invention, a feedstuff according to the invention or a composition used to produce a feedstuff according to the invention is preferably distinguished by the fact that it contains a biomass according to the invention in an amount of 1 to 25% by weight, preferably 2 to 20% by weight, in particular 3 to 15% by weight, above all 4 to 12% by weight.

Said feedstuff or the composition used to produce the feedstuff preferably additionally has at least one, preferably all, of the following properties:

a) a total protein content of 33 to 67% by weight, preferably 39 to 61% by weight, particularly 44 to 55% by weight;

b) a total fat content of 5 to 25% by weight, preferably 8 to 22% by weight, in particular 10 to 20% by weight, above all 12 to 18% by weight;

c) a total starch content of at most 25% by weight, in particular at most 20% by weight, preferably 6 to 17% by weight, especially preferably 8 to 14% by weight;

d) a polyunsaturated fatty acids (PUFAs) content of 2 to 13% by weight, preferably 3 to 11% by weight, in particular 4 to 10% by weight, above all 5.5 to 9% by weight;

e) an omega-3 fatty acids content of 1 to 7% by weight, preferably 1.5 to 5.5% by weight, in particular 2 to 5% by weight, above all 2.5 to 4.5% by weight;

f) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

The invention therefore preferably also provides a feedstuff or a composition suitable for producing the feedstuff having at least one, preferably all, of the following properties:

a) a total protein content of 33 to 67% by weight, preferably 39 to 61% by weight, in particular 44 to 55% by weight;

b) a total fat content of 5 to 25% by weight, preferably 8 to 22% by weight, in particular 10 to 20% by weight, above all 12 to 18% by weight;

c) a total starch content of at most 25% by weight, in particular at most 20% by weight, preferably 6 to 17% by weight, especially preferably 8 to 14% by weight;

d) a polyunsaturated fatty acids (PUFAs) content of 2 to 13% by weight, preferably 3 to 11% by weight, in particular 4 to 10% by weight, above all 5.5 to 9% by weight;

e) an omega-3 fatty acids content of 1 to 7% by weight, preferably 1.5 to 5.5% by weight, in particular 2 to 5% by weight, above all 2.5 to 4.5% by weight;

f) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

The invention therefore preferably also provides a feedstuff or a composition suitable for producing the feedstuff having at least one, preferably all, of the following properties:

a) a total protein content of 33 to 67% by weight, preferably 39 to 61% by weight, in particular 44 to 55% by weight;

b) a total fat content of 5 to 25% by weight, preferably 8 to 22% by weight, in particular 10 to 20% by weight, above all 12 to 18% by weight;

c) a total starch content of at most 25% by weight, in particular at most 20% by weight, preferably 6 to 17% by weight, especially preferably 8 to 14% by weight;

d) a content of biomass according to the invention, in particular a Labyrinthulea biomass according to the invention, preferably a Thraustochytriaceae biomass according to the invention, of 2 to 24% by weight, preferably 4 to 22% by weight, in particular 9 to 20% by weight, above all 11 to 18% by weight;

e) a polyunsaturated fatty acids (PUFAs) content of 2 to 13% by weight, preferably 3 to 11% by weight, in particular 4 to 10% by weight, above all 5.5 to 9% by weight;

f) an omega-3 fatty acids content of 1 to 7% by weight, preferably 1.5 to 5.5% by weight, in particular 2 to 5% by weight, above all 2.5 to 4.5% by weight;

g) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

The invention therefore preferably also provides a feedstuff or a composition suitable for producing the feedstuff having at least one, preferably all, of the following properties:

a) a total protein content of 33 to 67% by weight, preferably 39 to 61% by weight, particularly 40 to 50% by weight;

b) a total fat content of 5 to 25% by weight, preferably 8 to 22% by weight, in particular 10 to 20% by weight, above all 12 to 18% by weight;

c) a total starch content of at most 25% by weight, in particular at most 20% by weight, preferably 6 to 17% by weight, especially preferably 8 to 14% by weight;

d) a content of an *Aurantiochytrium* or *Schizochytrium* biomass according to the invention, preferably an *Aurantiochytrium limacinum* biomass according to the invention, above all an *Aurantiochytrium limacinum* SR21 biomass according to the invention, of 1 to 25% by weight, preferably 2 to 20% by weight, in particular 3 to 15% by weight, above all 4 to 12% by weight;

e) a polyunsaturated fatty acids (PUFAs) content of 2 to 13% by weight, preferably 3 to 11% by weight, in particular 4 to 10% by weight, above all 5.5 to 9% by weight;

f) an omega-3 fatty acids content of 1 to 7% by weight, preferably 1.5 to 5.5% by weight, in particular 2 to 5% by weight, above all 2.5 to 4.5% by weight;

g) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

By extrusion of the aforementioned compositions, it is possible to obtain an extrudate. The present invention preferably provides said extrudates. In this connection, the extrusion of the feedstuff is preferably done at an energy input of 12-28 Wh/kg, in particular 14-26 Wh/kg, especially preferably 16-24 Wh/kg, above all 18-22 Wh/kg.

In this connection, a screw or twin-screw extruder is preferably employed in the extrusion process.

The extrusion process is preferably carried out at a temperature of 80-220° C., in particular 80-130° C., above all 95-110° C., a pressure of 10-40 bar, and a shaft rotational speed of 100-1000 rpm, in particular 300-700 rpm. The residence time of the mixture introduced is preferably 5-30 seconds, in particular 10-20 seconds.

The extrusion process may optionally comprise a compacting step and/or a compression step. It is preferred to intimately mix the components with each other before carrying out the extrusion process. This is preferably carried out in a drum equipped with vanes. In a preferred embodiment, this mixing step includes an injection of steam, in particular so as to bring about swelling of the starch which is preferably present. In this connection, the injection of steam is preferably carried out at a pressure of 1 to 5 bar, particularly preferably at a pressure of 2 to 4 bar.

Before being mixed with the algae biomass, the further feedstuff ingredients are preferably comminuted—if required—so as to ensure that a homogeneous mixture is obtained in the mixing step. The comminuting of the further feedstuff ingredients may be carried out, for example, using a hammer mill.

The extrudate created preferably has a diameter of 1 to 14 mm, preferably 2 to 12 mm, in particular 2 to 6 mm, and preferably also has a length of 1 to 14 mm, preferably 2 to 12 mm, in particular 2 to 6 mm. The length of the extrudate is set during extrusion by using a cutting tool. The length of the extrudate is preferably selected such that it approximately corresponds to the diameter of the extrudate. The diameter of the extrudate is defined by selecting the screen diameter.

In one embodiment preferred according to the invention, the extrusion process is followed by loading the extrudate obtained with oil. To this end, the extrudate is preferably first dried to a moisture content of not more than 5% by weight. According to the invention, the extrusion product may be loaded with oil by, for example, placing the extrudate in oil or spraying the extrudate with oil; however, according to the invention, preference is given to vacuum coating.

In this way, feedstuffs are obtained which contain biomasses according to the invention preferably in an amount of 1 to 25% by weight, in particular 2 to 20% by weight, especially preferably 3 to 15% by weight, above all 4 to 12% by weight.

Accordingly, said feedstuffs preferably additionally have at least one, preferably all, of the following properties:

a) a total protein content of 30 to 60% by weight, preferably 35 to 55% by weight, in particular 40 to 50% by weight;

b) a total fat content of 15 to 35% by weight, preferably 18 to 32% by weight, in particular 20 to 30% by weight, above all 22 to 28% by weight;

c) a total starch content of at most 25% by weight, in particular at most 20% by weight, preferably 5 to 15% by weight, especially preferably 7 to 13% by weight;

d) a polyunsaturated fatty acids (PUFAs) content of 2 to 12% by weight, preferably 3 to 10% by weight, in particular 4 to 9% by weight, above all 5 to 8% by weight;

e) an omega-3 fatty acids content of 1 to 6% by weight, preferably 1.5 to 5% by weight, in particular 2 to 4.5% by weight, above all 2.5 to 4% by weight;

f) a DHA content of 0.5 to 3% by weight, preferably 0.8 to 2.5% by weight, in particular 1 to 2.5% by weight, above all 1.2 to 2.2% by weight, in particular 1.2 to 2.0% by weight.

The invention therefore preferably also provides a feedstuff, in particular an extrudate, having at least one, preferably all, of the following properties:

a) a total protein content of 30 to 60% by weight, preferably 35 to 55% by weight, in particular 40 to 50% by weight;

b) a total fat content of 15 to 35% by weight, preferably 18 to 32% by weight, in particular 20 to 30% by weight, above all 22 to 28% by weight;

c) a total starch content of at most 25% by weight, in particular at most 20% by weight, preferably 5 to 15% by weight, especially preferably 7 to 13% by weight;

d) a polyunsaturated fatty acids (PUFAs) content of 2 to 12% by weight, preferably 3 to 10% by weight, in particular 4 to 9% by weight, above all 5 to 8% by weight;

e) an omega-3 fatty acids content of 1 to 6% by weight, preferably 1.5 to 5% by weight, in particular 2 to 4.5% by weight, above all 2.5 to 4% by weight;

f) a DHA content of 0.5 to 3% by weight, preferably 0.8 to 2.5% by weight, in particular 1 to 2.5% by weight, above all 1.2 to 2.2% by weight, in particular 1.2 to 2.0% by weight.

The invention therefore preferably also provides a feedstuff, in particular an extrudate, having at least one, preferably all, of the following properties:

a) a total protein content of 30 to 60% by weight, preferably 35 to 55% by weight, in particular 40 to 50% by weight;

b) a total fat content of 15 to 35% by weight, preferably 18 to 32% by weight, in particular 20 to 30% by weight, above all 22 to 28% by weight;

c) a total starch content of at most 25% by weight, in particular at most 20% by weight, preferably 5 to 15% by weight, especially preferably 7 to 13% by weight;

d) a content of a biomass according to the invention, in particular a Labyrinthulea biomass according to the invention, preferably a Thraustochytriaceae biomass according to the invention, of 1 to 25% by weight, preferably 2 to 20% by weight, in particular 3 to 15% by weight, above all 4 to 12% by weight;

e) a polyunsaturated fatty acids (PUFAs) content of 2 to 12% by weight, preferably 3 to 10% by weight, in particular 4 to 9% by weight, above all 5 to 8% by weight;

f) an omega-3 fatty acids content of 1 to 6% by weight, preferably 1.5 to 5% by weight, in particular 2 to 4.5% by weight, above all 2.5 to 4% by weight;

g) a DHA content of 0.5 to 3% by weight, preferably 0.8 to 2.5% by weight, in particular 1 to 2.5% by weight, above all 1.2 to 2.2% by weight, in particular 1.2 to 2.0% by weight.

The invention therefore preferably also provides a feedstuff, in particular an extrudate, having at least one, preferably all, of the following properties:

a) a total protein content of 30 to 60% by weight, preferably 35 to 55% by weight, particularly 40 to 50% by weight;

b) a total fat content of 15 to 35% by weight, preferably 18 to 32% by weight, in particular 20 to 30% by weight, above all 22 to 28% by weight;

c) a total starch content of at most 25% by weight, in particular at most 20% by weight, preferably 5 to 15% by weight, especially preferably 7 to 13% by weight;

d) a content of an *Aurantiochytrium* or *Schizochytrium* biomass according to the invention, preferably an *Aurantiochytrium limacinum* biomass according to the invention, above all an *Aurantiochytrium limacinum* SR21 biomass according to the invention, of 1 to 25% by weight, preferably 2 to 20% by weight, in particular 3 to 15% by weight, above all 4 to 12% by weight;

e) a polyunsaturated fatty acids (PUFAs) content of 2 to 12% by weight, preferably 3 to 10% by weight, in particular 4 to 9% by weight, above all 5 to 8% by weight;

f) an omega-3 fatty acids content of 1 to 6% by weight, preferably 1.5 to 5% by weight, in particular 2 to 4.5% by weight, above all 2.5 to 4% by weight;

g a DHA content of 0.5 to 3% by weight, preferably 0.8 to 2.5% by weight, in particular 1 to 2.5% by weight, above all 1.2 to 2.2% by weight, in particular 1.2 to 2.0% by weight.

According to the invention, the fat-containing component used may be, besides the biomass to be used according to the invention, fats, in particular oils, of both animal and plant origin. According to the invention, suitable fat-containing components are in particular vegetable oils, for example soya bean oil, rapeseed oil, sunflower seed oil, flaxseed oil or palm oil and mixtures thereof. In addition, fish oil may also optionally be used as fat-containing component in low amounts.

According to the invention, the protein-containing component used may be, for example, soya protein, pea protein, wheat gluten or corn gluten and mixtures thereof.

The following examples may be employed as a protein-containing component which additionally contains fats: fish meal, krill meal, mussel meal, squid meal or shrimp shells. These are hereinbelow subsumed under the term "marine meal". In a preferred embodiment, a feedstuff according to the invention comprises marine meal, preferably fish meal, in an amount of 3 to 18% by weight, in particular 5 to 15% by weight, above all 7 to 13% by weight.

The carbohydrate-containing component used may be, for example, wheat meal, sunflower meal or soya meal and mixtures thereof.

When using feedstuffs according to the invention, in particular an oil-coated extrudate according to the invention, in animal farming, it became apparent that this especially promotes the growth of the animals and improves the stress level of the animals.

The present invention also further provides a method for farming animals, characterized in that they are administered a feedstuff according to the invention.

In this connection, the present invention provides in particular a method for increasing the growth of animals, characterized in that they are administered a feedstuff according to the invention.

The present invention further provides in particular similarly a method for increasing the fraction of omega-3 fatty acids, in particular DHA, in the muscle tissue of animals, characterized in that they are administered a feedstuff according to the invention.

Preferably, in the method according to the invention, the feedstuff is administered at least every two days, preferably at least once daily.

The present invention further provides similarly the use of a feedstuff according to the invention for increasing growth in animals.

The present invention further provides likewise the use of a feedstuff according to the invention for increasing the fraction of omega-3 fatty acids in muscle tissue in animals.

The present invention further provides likewise the use of a feedstuff according to the invention for improving the physical condition of animals, in particular for improving the stress level of animals.

The present invention further provides likewise the use of a feedstuff according to the invention for allowing a stress-reduced farming of the animals.

The farmed animals fed with a feedstuff according to the invention are preferably poultry, pigs or cattle.

However, the farmed animals are especially preferably marine animals, especially preferably finfish or crustaceans. These include, in particular, carp, tilapia, catfish, tuna, salmon, trout, barramundi, bream, perch, cod, shrimps, lobster, crabs, prawns and crayfish. The farmed animals are especially preferably salmon. Preferred types of salmon in this context are the Atlantic salmon, red salmon, masu salmon, king salmon, keta salmon, coho salmon, Danube salmon, Pacific salmon and pink salmon.

The farmed animals may in particular also be fish which are subsequently processed into fish meal or fish oil. In this connection, the fish are preferably herring, pollack, menhaden, anchovies, capelin or cod. The fish meal or fish oil thus obtained, in turn, can be used in aquaculture for farming edible fish or crustaceans.

However, the farmed animals may also be small organisms which are used as feedstuff in aquaculture. These small organisms may take the form of, for example, nematodes, crustaceans or rotifers.

The farming of marine animals may take place in ponds, tanks, basins or else in segregated areas in the sea or in lakes, in particular in this case in cages or net pens. Farming may be used for farming the finished edible fish, but also may be used for farming fry which are subsequently released so as to restock the wild fish stocks.

In salmon farming, the fish are preferably first grown into smolts in freshwater tanks or artificial watercourses and then grown on in cages or net pens which float in the sea and which are preferably anchored in bays or fjords.

Accordingly, the feedstuff according to the invention is preferably a feedstuff for use in the farming of the above-mentioned animals.

EXEMPLARY EMBODIMENTS

Example 1

Producing Biomass by Fermentation of
*Aurantiochytrium Limacinum* SR21 in a Medium
having a High Sulfate Content and Subsequent
Drying of the Biomass The cells were cultured for about 70 h in a feed process using a steel fermenter having a fermenter volume of 2 litres with a total starting mass of about 700 g and an attained total final mass of about 1.5 kg. During the process, a glucose solution (570 g/kg glucose) was metered in ("fed-batch process").

The composition of the starting medium was as follows:

Medium 1: 20 g/kg glucose; 4 g/kg yeast extract; 2 g/kg ammonium sulfate; 12 or 16 g/kg sodium sulfate; 2.46 g/kg magnesium sulfate (heptahydrate); 0.45 g/kg potassium chloride; 4.5 g/kg potassium dihydrogen phosphate; 0.1 g/kg thiamine (HCl); 5 g/kg trace element solution.

The composition of the trace element solution was as follows: 35 g/kg hydrochloric acid (37%); 1.86 g/kg manganese chloride (tetrahydrate); 1.82 g/kg zinc sulfate (heptahydrate); 0.818 g/kg sodium EDTA; 0.29 g/kg boric acid; 0.24 g/kg sodium molybdate (dihydrate); 4.58 g/kg calcium chloride (dihydrate); 17.33 g/kg iron sulfate (heptahydrate); 0.15 g/kg copper chloride (dihydrate). Culturing was carried out under the following conditions: Culture temperature 28° C.; aeration rate 0.5 wm, stirrer speed 600-1950 rpm, control of pH in the growth phase at 4.5 using ammonia water (25% v/v). Fermentation was carried out up to a biomass density of 80 g/l before the oil-production phase was introduced by limitation of phosphate and nitrogen. Because of the high sulfate content in the starting medium until the end of fermentation, i.e. including until the end of the oil-production phase, the sulfate concentration is always above the saturation limit of the cells, which is about 5 g per kg of dry biomass. The biomasses obtained are hereinafter referred to as "Biomass 1" (12 g/kg sodium sulfate in the starting medium) and "Biomass 2" (16 g/kg sodium sulfate in the starting medium).

The sulfate content of the biomass obtained was determined by determining the sulfur content of the biomass in accordance with DIN ISO 11885.

Example 2

Producing Biomass by Fermentation of *Aurantiochytrium Limacinum* SR21 in a Medium having a Low Sulfate Content and Subsequent Drying of the Biomass The cells were cultured for about 70 h in a feed process using a steel fermenter having a fermenter volume of 2 litres with a total starting mass of 712 g and an attained total final mass of about 1.5 kg. During the process, a glucose solution (570 g/kg glucose) was metered in ("fed-batch process").

The composition of the starting medium was as follows:

Medium 1: 20 g/kg glucose; 4 g/kg yeast extract; 0 g/kg ammonium sulfate; 2.46 g/kg magnesium sulfate (heptahydrate); 0.45 g/kg potassium chloride; 4.5 g/kg potassium dihydrogen phosphate; 0.1 g/kg thiamine (HCl); 5 g/kg trace element solution.

The composition of the trace element solution was as follows: 35 g/kg hydrochloric acid (37%); 1.86 g/kg manganese chloride (tetrahydrate); 1.82 g/kg zinc sulfate (heptahydrate); 0.818 g/kg sodium EDTA; 0.29 g/kg boric acid; 0.24 g/kg sodium molybdate (dihydrate); 4.58 g/kg calcium chloride (dihydrate); 17.33 g/kg iron sulfate (heptahydrate); 0.15 g/kg copper chloride (dihydrate). Culturing was carried out under the following conditions: Culture temperature 28° C.; aeration rate 0.5 wm, stirrer speed 600-1950 rpm, control of pH in the growth phase at 4.5 using ammonia water (25% v/v). Fermentation was carried out up to a biomass density of 80 g/l before the oil-production phase was introduced by limitation of phosphate and nitrogen. The sulfate concentration had already fallen below the detection limit of 0.05 g per kg of fermentation medium upon introduction of the oil-production phase, and the sulfate concentration was accordingly also below the detection limit during the entire oil-production phase. And since there was no metered addition of sulfate, the sulfate concentration fell to zero in the course of the oil-production phase. The biomass obtained is hereinafter referred to as "Biomass 3".

Example 3

Work-Up and Comparison of the Biomasses Obtained and of the Processes

After the culturing process, the fermentation broths were heated to 60° C. for 20 minutes in order to prevent further cellular activity.

This was followed by a two-stage drying of the biomass: Firstly, the fermentation broth was concentrated by evaporation to a dry mass of about 20% by weight. Thereafter, the concentrated fermentation broth was spray-dried using a Production Minor™ Spray Dryer (GEA NIRO) at an inlet temperature of the drying air of 340° C. Spray-drying thus gave a powder with more than 95% by weight of dry mass.

16

TABLE 1

| Comparison of the biomasses obtained | | | | |
| --- | --- | --- | --- | --- |
| Bio-mass | Sulfate content [g/kg] (sulfate per kg biomass) | Yield [%] (g DHA per g dextrose) | Product, total [g] (g DHA) | Purity [%] (g DHA per g dry biomass) |
| 1 | 29.7 | 7.8 | 44.2 | 15.7 |
| 2 | 32.5 | 7.3 | 45.4 | 15.4 |
| 3 | 8.4 | 7.1 | 35.5 | 20.1 |

Biomasses 1 and 2 are biomasses obtained by fermentation at high sulfate content as per Example 1; by contrast, Biomass 3 is a biomass obtained by fermentation at low sulfate content as per Example 2.

It can be discerned that the fermentation process which was carried out at low sulfate content and led to Biomass 3 delivered a product having distinctly higher purity, i.e. a product having a distinctly increased proportion of DHA, than those processes which were carried out at high sulfate content and led to Biomasses 1 and 2. In addition, the sulfate content in the biomass obtained is also distinctly lower than in the case of the process with high sulfate content.

The invention claimed is:

1. A process for producing a biomass containing polyunsaturated fatty acids (PUFAs) by fermentation, said fermentation comprising: a) a growth phase wherein Thraustochytriaceae cells are incubated in a fermentation medium comprising sulfate and nutrients needed for cell growth other than sulfate; b) an oil-production phase that begins after sulfate in the growth phase falls below 0.05 g per kg of fermentation medium and that is initiated by limiting at least one of said nutrients needed for cell growth other than sulfate; wherein sulfate in the fermentation medium is at a concentration that remains below 0.05 g/kg throughout the oil-production phase; and at the beginning of the growth phase a concentration of sulfate is present in an amount such that there is a sulfate concentration of 7.5 to 9.5 g per kg of biomass at the end of the oil-production phase.

2. The process of claim 1, wherein sulfate at the beginning of the growth phase is present in an amount such that there is a sulfate concentration of 7.5 to 9.5 g per kg of biomass at the end of the oil-production phase.

3. The process of claim 1, comprising as a further step, a mechanical disruption of the biomass obtained at the end of the oil-production phase, using a mechanical force of up to 12 Watt-hours per kilogram (Wh/kg).

4. The process of claim 1, comprising, as a further step, a mechanical disruption of the biomass obtained at the end of the oil-production phase, using a mechanical force of 1 to 10 Wh/kg.

5. The process of claim 1; wherein the sulfate concentration in the fermentation medium falls to below 0.05 g per kg of fermentation medium in the second half of the growth phase.

6. The process of claim 1, wherein the fermentation produces a broth that is concentrated and further processed to give a feedstuff.

7. The process of claim 1, wherein, in the growth phase, cells are cultured to a biomass density of at least 50 g per litre of fermentation medium.

8. The process of claim 7, wherein, in the growth phase, sulfate concentration in the medium falls below 0.05 g per kg after a biomass density of at least 50 g per litre of fermentation medium has been reached.

9. The process of claim 1, wherein the cells are cultured in the growth phase to a biomass density of at least 100 g per litre of fermentation medium.

10. The process of claim 9, wherein the limiting nutrient is nitrogen.

11. The process of claim 1, wherein the fermentation medium contains a chloride content of not more than 2 g per kg during the entire fermentation.

12. The process of claim 1, wherein the fermentation medium contains a chloride content of not more than 500 mg/L during the entire fermentation.

13. The process of claim 1, wherein the fermentation medium contains a chloride content of not more than 250 mg/L during the entire fermentation.

14. The process of claim 1, wherein the cells are of the genus *Thraustochytrium, Schizochytrium, Aurantiochytrium* or *Oblongichytrium.*

15. The process of claim 1, wherein the concentration of sulfate at the beginning of the growth phase is adjusted using sodium sulfate.

16. The process of claim 15, wherein the oil production phase is initiated by limiting nitrogen.

17. The process of claim 1, wherein the cells in the biomass obtained contain at least 40% by weight of PUFAs, based on dry biomass.

18. The process of claim 17, wherein the cells are *Schizochytrium* or *Aurantiochytrium* cells.

19. A process for producing a biomass containing polyunsaturated fatty acids (PUFAs) by fermentation, said fermentation comprising: a) a growth phase wherein Thraustochytriaceae cells are incubated in a fermentation medium comprising sulfate and nutrients needed for cell growth other than sulfate wherein: i) the sulfate concentration at the beginning of the growth phase is chosen, at least in part, to optimize purity based on grams of docosahexaenoic acid (DHA) per kg of dry biomass in cells when an oil-production phase is complete; and ii) the cells are cultured in the growth phase up to a biomass density of 50 to 250 g per litre of fermentation medium; and b) an oil-production phase, wherein said oil-production phase begins after sulfate in the growth phase falls below 0.05 g per kg of fermentation medium and that is initiated by limiting nitrogen or phosphate; wherein sulfate in the fermentation medium is at a concentration that remains below 0.05 g/kg throughout the entire oil-production phase and there is a chloride content of not more than 250 mg/L during the entire fermentation; and at the beginning of the growth phase a concentration of sulfate is present in an amount such that there is a sulfate concentration of 7.5 to 9.5 g per kg of biomass at the end of the oil-production phase.

\* \* \* \* \*